United States Patent
Bassez et al.

(10) Patent No.: US 7,966,197 B2
(45) Date of Patent: Jun. 21, 2011

(54) DEVICE FOR ASSISTANCE IN THE SELECTION OF A COMPRESSION ORTHOSIS AND IN ADAPTING SAME TO THE MORPHOLOGY OF A LIMB

(75) Inventors: Sophie Bassez, Villebon sur Yvette (FR); Jean-Louis Testud, Paris (FR)

(73) Assignee: Laboratoires Innothera, Arcueil (FR)

( * ) Notice: Subject to any disclaimer, the term of this patent is extended or adjusted under 35 U.S.C. 154(b) by 1273 days.

(21) Appl. No.: 10/553,877

(22) PCT Filed: Apr. 21, 2004

(86) PCT No.: PCT/FR2004/000976
§ 371 (c)(1),
(2), (4) Date: Sep. 5, 2006

(87) PCT Pub. No.: WO2004/095342
PCT Pub. Date: Nov. 4, 2004

(65) Prior Publication Data
US 2007/0055537 A1 Mar. 8, 2007

(30) Foreign Application Priority Data
Apr. 22, 2003 (FR) .................................. 03 04931

(51) Int. Cl.
*G06F 19/00* (2011.01)

(52) U.S. Cl. ........................................................ 705/3

(58) Field of Classification Search .................. 705/2, 3; 73/831; 602/17
See application file for complete search history.

(56) References Cited

U.S. PATENT DOCUMENTS

| 6,383,148 B1 | 5/2002 | Pusch et al. |
| 6,499,356 B1 * | 12/2002 | Flaud et al. ........................ 73/831 |
| 2002/0010408 A1 * | 1/2002 | Pomatto et al. ................. 602/17 |

FOREIGN PATENT DOCUMENTS

| FR | 2774276 | 8/1999 |
| FR | 2804595 | 8/2001 |
| WO | WO 01/11337 | 2/2001 |

OTHER PUBLICATIONS

Chu, T., et al., "Three-dimensional finite element stress analysis of the polypropylene, ankle-foot orthosis: statis analysis," Medical Engineering & Physics, UK, Jul. 1995, vol. 17, No. 5, pp. 372-379, [XP002277428].

(Continued)

*Primary Examiner* — Gerald J. O'Connor
*Assistant Examiner* — John A Pauls
(74) *Attorney, Agent, or Firm* — Jacobson Holman PLLC

(57) ABSTRACT

The invention relates to a device for assistance in the selection of a compression orthosis and in adapting same to the morphology of a limb. The inventive device consists of: means (26) for establishing a first file containing data representative of the morphological characteristics of the limb (30), comprising the three-dimensional co-ordinates of a mesh of points (68) with different heights; means (10) for establishing a second file containing data representative of the dimensional and rheological characteristics of the orthesis, which are defined with different heights; compression simulation means (48) which, using the data from the first and second files, can determine the compression pressure values that are likely to be exerted by the orthesis on the limb at a plurality of points of said mesh; and means (50) for displaying the pressure values thus determined in a graphical manner, for example, by overlaying a 3D graphical representation of the limb, or a section of same, with the false color- or grey level-coded calculated pressure.

9 Claims, 4 Drawing Sheets

OTHER PUBLICATIONS

Syngellakis, S., et al., "Assessment of the non-linear behaviour of plastic ankle foot orthoses by the finite element method," Proceedings of the Institution of Mechanical Engineers, Part H (Journal of Engineering in Medicine), UK, 2000, vol. 214, No. H5, pp. 527-539, [XP001161162].

Hanafusa, A., et al., "Computer assisted orthosis design system for malformed ears-automatic shape modification method for preventing excessive corrective force," Proceedings of the 22nd Annual Int'l. Conference of the IEEE Engineering in Medicine and Biology Society (CAT. No. 00CH37143), Chic., 2000, vol. 3, pp. 1976-1978, [XP002277429].

Buckley, M., et al., "Computer simulation of the dynamics of a human arm and orthosis linkage mechanism," Proceedings of the Institution of Mechanical Engineers, Part H (Journal of Engineering in Medicine), UK, 1997, vol. 211, No. H5, pp. 349-357, [XP001161163].

\* cited by examiner

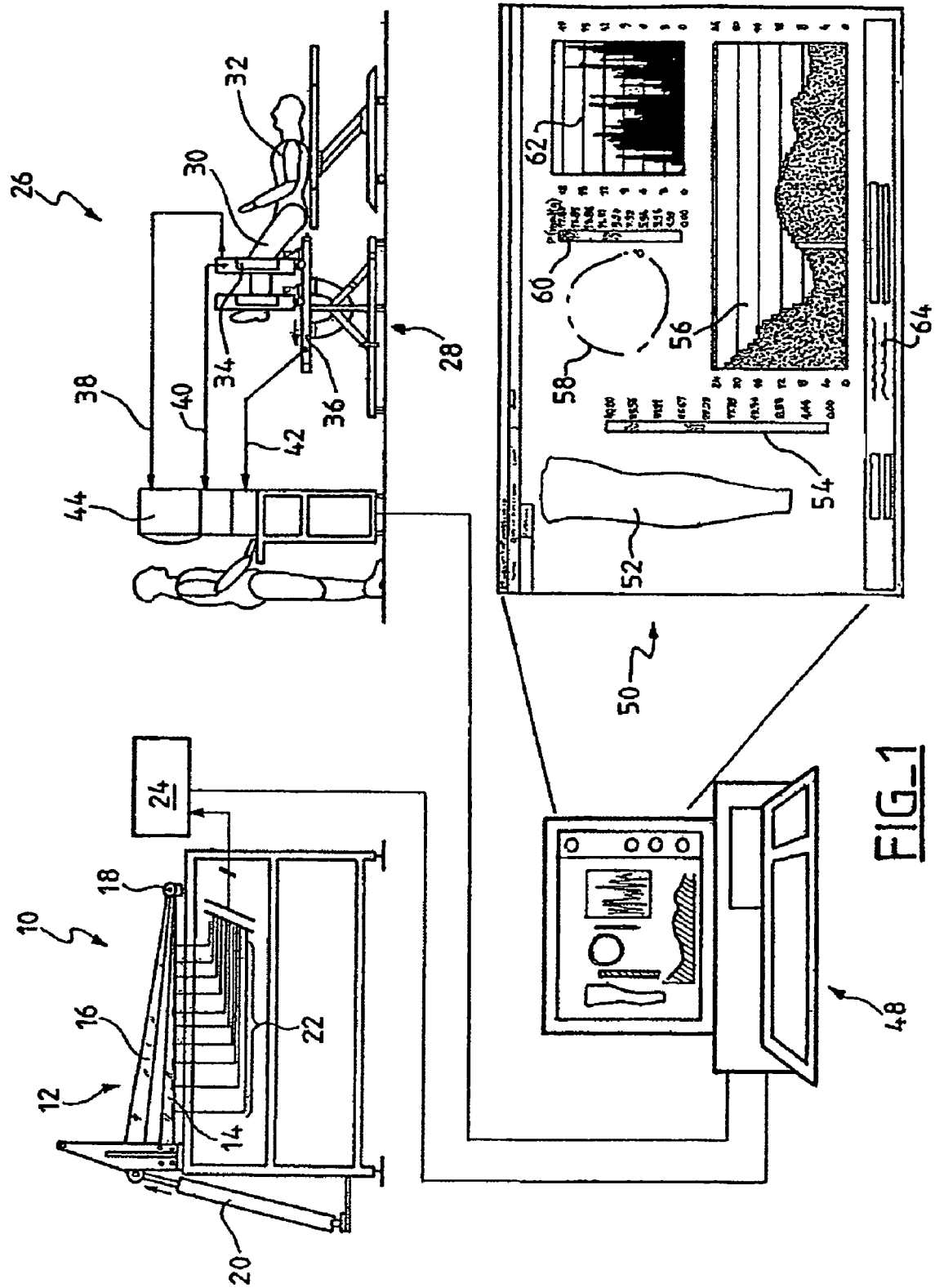
FIG_1

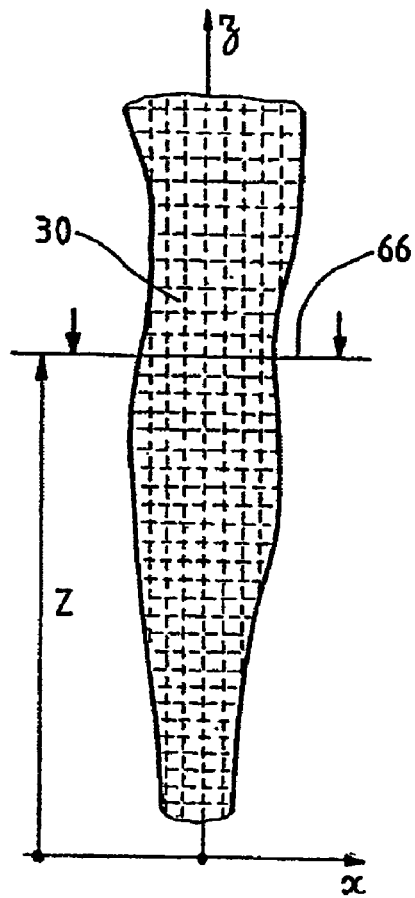
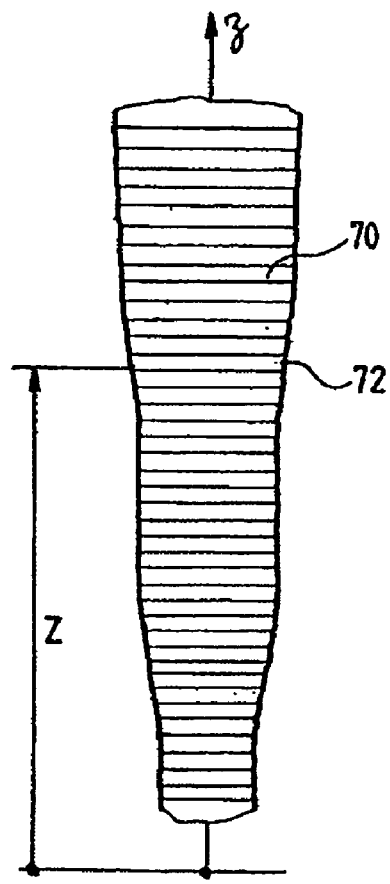
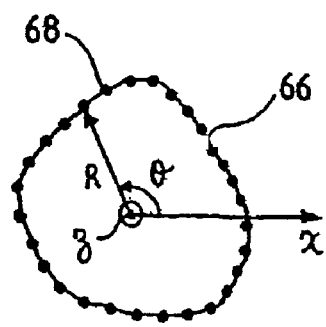
FIG_2
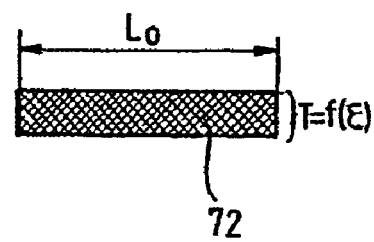
FIG_3

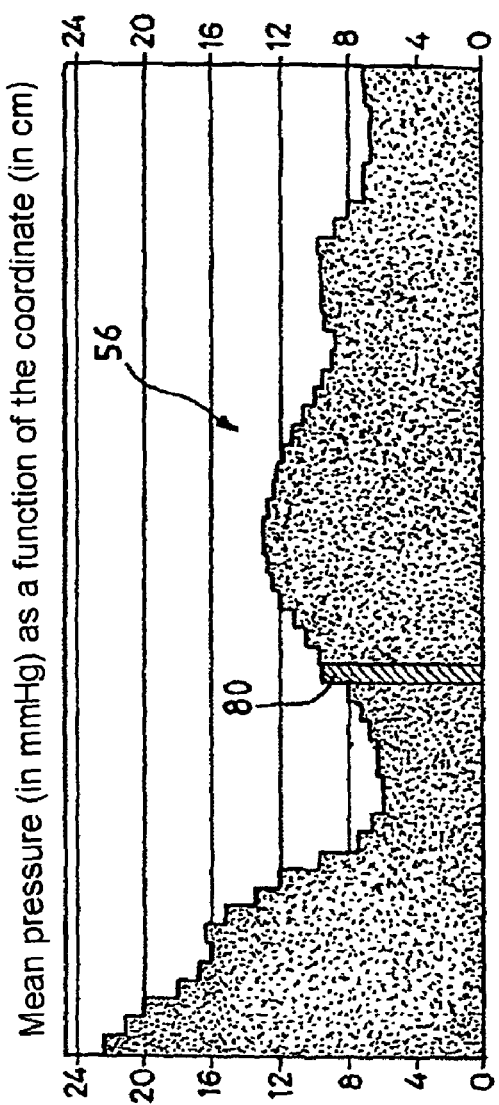
FIG_5
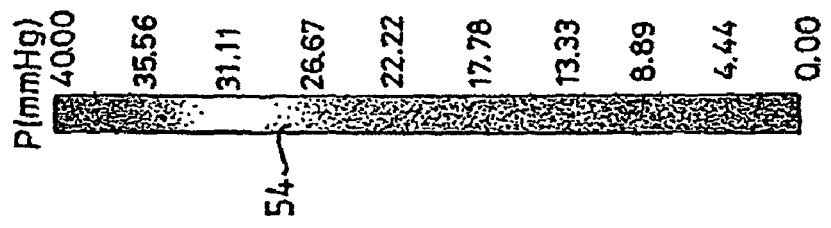
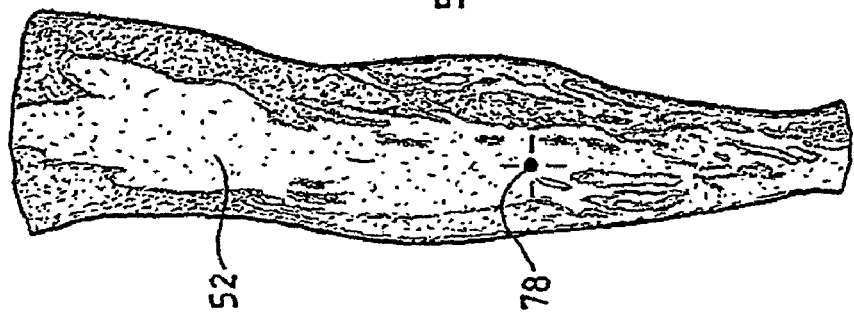
FIG_4

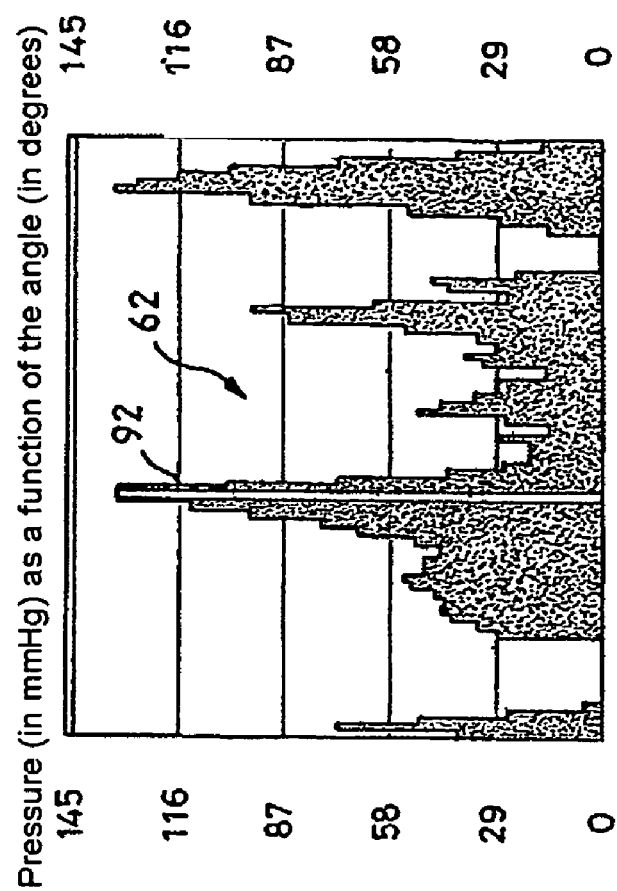
FIG_7
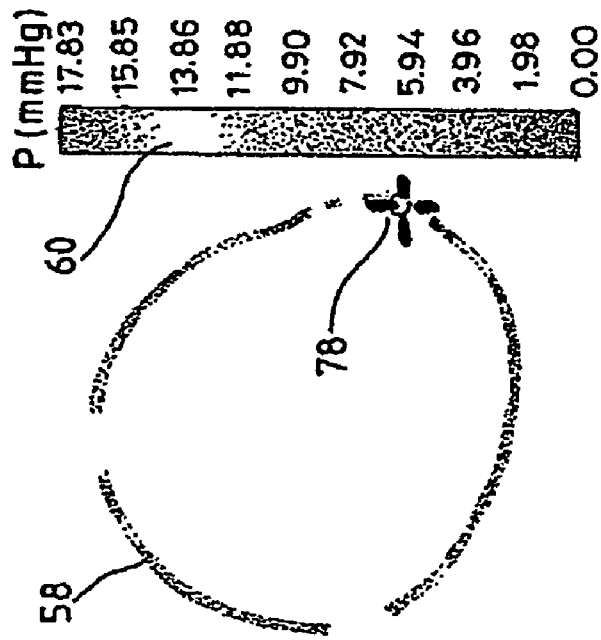
FIG_6

DEVICE FOR ASSISTANCE IN THE SELECTION OF A COMPRESSION ORTHOSIS AND IN ADAPTING SAME TO THE MORPHOLOGY OF A LIMB

This is a 371 of PCT/FR04/000976, filed 21 Apr. 2004.

The invention concerns a device for assistance in the selection of a compression orthosis and in adapting same to the morphology of a limb for which that orthosis is intended. The invention more precisely concerns tubular compressive orthoses and bandages made from knitted elastic and non-elastic textile materials.

These orthoses can take several forms. For example, in the case of compressive orthoses for one or both lower limbs, it may concern stockings in the strict sense (covering the thigh and the calf), pantyhose (covering both lower limbs and the abdomen up to the waist, in one piece), single-leg pantyhose (pantyhose with only one leg, intended for the compression of only one of the lower limbs) or socks (covering only the calf). The term "stocking" will be used hereinafter although the invention is not limited to one particular article, but applies equally to all compressive orthoses. The invention may also be applied to compressive orthoses intended for the upper limbs.

To enable strong compression of the limb or limbs, these orthoses are made from an elastic material, typically a fine mesh knitted material achieving the required therapeutic effect, namely compression to a therapeutic degree, with degression from the ankle.

Medical compression stockings are stockings that exert a pressure, as measured at the ankle, from 10 to more than 36 mmHg (13 to 48 hPa; millimeters of mercury are nevertheless used in the present description as a unit of measurement of pressure given their universal use in the field of phlebology and medical compression).

One problem for the prescribing practitioner, especially with orthoses of the higher compressive classes, is choosing a size and a class of orthosis best adapted to the pathology of the patient, i.e. achieving compression that is neither too weak nor too strong over the whole extent of the limb.

Moreover, unless a stocking is made to measure, the practitioner must choose for his prescription a particular size from pre-existing ranges of sizes, for which the pressures applied by the various articles from these ranges are established relative to a template of standardized shape and dimensions (known as the "Hohenstein model").

An orthosis size is obtained by measuring the leg of the patient at different heights, for example three perimeter measurements at the ankle, the calf and the thigh, as well as the ground-knee and ground-crotch heights. From these measurements, the pharmacist or orthopaedist determines the size of the article most appropriate for the patient from a table or a scale.

This procedure is somewhat empirical, however, and in any event does not give the prescribing doctor a real idea of the pressure profile that will actually be applied to the leg, in particular for patients whose leg morphology is far from the standardized shape. Prescribing an inappropriate orthosis may be reflected in certain localized areas of excessive or, conversely, insufficient compression.

One object of the invention is to remedy this problem by proposing a device enabling the practitioner to evaluate the adaptation of an orthosis size to the morphology of the leg of a given patient so as to be able to choose on an informed basis that which is liable to achieve the optimum therapeutic affect for that patient.

Another object of the invention is to propose a tool which, in the context of a clinical study of a population of patients, determines whether the existing range of different sizes of a given product is well adapted to the majority of that population or, on the contrary, that a range of different sizes would be more appropriate for covering the requirements of the greatest number of patients.

To this end, the device of the invention comprises: means for establishing a first file containing data representative of the morphological characteristics of the limb, this first data file comprising the coordinates, in a three-dimensional space, of a array of points distributed on the surface of the limb along a succession of contours defined at different successive coordinates of that limb; means for establishing a second file containing data representative of the dimensional and rheological characteristics of the orthosis defined at different successive coordinates of that orthosis; compression simulation means able to determine, using data from the first and second files, compression pressure values that are liable to be exerted by the orthosis on the limb at a plurality of points of said array; and means for displaying said pressure values determined by the compression simulation means.

The second data file may in particular contain data for the flat width of the orthosis at said successive coordinates and data representative of the deformation characteristic of the orthosis as a function of the tension exerted thereon between points situated at consecutive coordinates.

The device advantageously comprises designation means enabling an operator of the device to designate a point of the array and to command the pressure value display means to display the value of the pressure calculated at the designated point, and/or designation means enabling an operator of the device to designate a coordinate of the array and to command the pressure value display means to display the pressure value calculated at the various points of the contour of the section of the limb situated at the designated coordinate.

The display means preferably comprise graphical means able to display a three-dimensional graphical representation of the limb and to associate locally with that graphical representation the pressure values calculated at the various points of said array and/or graphical means able to display a two-dimensional graphical representation of a section of the limb and to associate locally with that graphical representation the pressure values calculated at the various points of the contour of that section.

In an advantageous embodiment, the graphical means associate the calculated pressure values with the graphical representation by superimposing a coding by grey levels or false colours of the pressure calculated at those points on said graphical representation at the location of the various points.

The display means may comprise graphical means able to display a characteristic giving the variation as a function of angular position of the pressure calculated at the various points of the contour of a section of the limb situated at a given coordinate.

In a comparable manner, the simulation means are able to determine average values of the compression pressure at points situated at the same coordinate, and also their associated standard deviations, where appropriate, the display means comprising graphical means able to display a characteristic giving the variation as a function of the coordinate of the calculated mean compression pressure.

One embodiment of the invention will now be described with reference to the appended drawings.

FIG. 1 is a diagram showing the various means contributing to the implementation of the invention.

FIG. 2 shows modelling the leg of the patient.

FIG. 3 shows modelling the orthosis.

FIGS. 4 to 7 show how it is possible to display in graphical form the effects that the orthosis is liable to produce on the leg of the patient.

FIG. 1 is a general representation of the various means for evaluating the effects of the compression of a particular orthosis on a precise leg morphology.

It is necessary first of all to model in digital form the dimensional and rheological characteristics of the orthosis.

The rheological law (i.e. the relation between the tension applied to the product and the resulting radial deformation) can in particular be determined by means of an extensometer 10 such as that described in WO-A-01/11337 (Innothéra Topic International), which includes a form 12 adapted to have an orthosis threaded over it, with two elongate branches 14, 16 articulated at 18 in the manner of a compass. The branches may be moved apart in a controlled manner by an actuator 20 and sensors 22 distributed along the length of a branch measure the radial tension applied over the whole length of the orthosis under the radial extension load applied by the actuator 20. These various measurements are digitized by a device 24, which produces data for evaluating the rheological law of the orthosis over the whole length thereof by modelling and/or interpolation.

Where the morphology of the leg is concerned, the shape thereof may be established by diverse means known in themselves.

An installation 26 such as that described in FR-A-2 774 276 and FR-A-2 804 595 (Innothéra Topic International), which describe a laser plethysmograph 28 for establishing a very accurate map of a limb 30 of a subject 32 along successive sections of that limb may be used, for example. The plethysmograph 28 includes a ring of sensors 34 for analyzing by triangulation the shape of a section of the leg placed in the central space of this ring. The latter can be moved in translation along a linear axis 36, by successive steps, to reiterate the measurement for different sections over the whole length of the limb 30. The measurement signals and the positions of the circular axis and the linear axis are transmitted by connections 38, 40, 42 to a device 44 for reconstituting from this information a three-dimensional representation of the leg 30 in the form of a set of regularly spaced parametered curves.

After defining the dimensional and rheological characteristics of the orthosis and the morphological characteristics of the limb in this way, the corresponding data is stored in respective files of a computer 48 and is then compared to determine the compression pressure values liable to be exerted on the limb.

These pressure values are advantageously presented to the practitioner in the form of a graphical display 50 including, for example (the various components of this display will be described in more detail with reference to FIGS. 4 to 8):

a three-dimensional view 52 of the leg, in which the pressures are coded in grey levels or false colours against a pressure scale 54, a characteristic 56 giving the variation of the average pressure, section by section, over the length of the leg from the ankle to the thigh, a two-dimensional representation 58 of a leg section at a level chosen by the practitioner, also coded in grey levels or false colours against a corresponding scale 60, a characteristic 62 giving the angular distribution of the pressures over the section represented at 58, and a digital information area 64 corresponding to certain particular points designated on the representation 52 or 58.

There will now be described, with reference to FIGS. 2 and 3, how respective data files representing the morphological characteristics of the limb and the dimensional and rheological characteristics of the orthosis are constituted.

Where the limb 30 is concerned (FIG. 2), the data is defined for a series of sections 66 with successive coordinates Z, this data being determined, for example, by the position of points 68 defined by their coordinate Z and their polar coordinates R, θ relative to a system of axes (Ox, Oz). The measurement coordinates must at the very least comprise the co-ordinates corresponding to the standardized heights b, b1, c, d, e, f and g of a Hohenstein leg, the origin of the system of axes in the direction z being on the floor at Z=0, so as to obtain a vertical reference common to the leg and to the orthosis.

Depending on the required accuracy of the measurements, there is produced in this way a coarser or finer meshing of the leg, in which each node of the array is identified by its coordinates Z, r, θ.

Starting from this position data for the various points of the array, the next step consists in determining for each section the perimeter C and the curvature c at any point of that section from the coordinates of the points of the contour, using methods known in themselves.

As far as the orthosis 70 (FIG. 3) is concerned, it is first of all necessary to determine its dimensional characteristics.

Being a product that can be laid out flat, there is advantageously used the unstretched flat width $L_0$ of the product at different coordinates Z defining a plurality of measurement levels 72. The measurement points, at the very least those corresponding to the standardized heights b, b1, c, d, e, f and g of a Hohenstein leg, are identified on the orthosis 70 relative to the heel (origin at floor level with coordinate Z=0).

The rheological characteristics, i.e. the law giving the longitudinal deformation $\epsilon$ as a function of the applied tension T, can be determined either by dynamometer measurements or, as described with reference to FIG. 1, by using an extensometer under the conditions defined above, the elongation $\epsilon$ being calculated as the ratio of the application length to the unstretched length. From these measurements there is extrapolated a law for determining the tension as a function of the deformation at any point on the orthosis.

From data collected and stored in this way, the device then calculates the compression pressure that the orthosis 70 would exert on the leg 30, as modelled, if it were threaded over the latter. This compression pressure is calculated for each section of the leg (associated with a coordinate Z relative to the floor), at the various points of the contour of that section. The theory of calculating the compression pressure at a given point is based on the application of Laplace's law P=T.c, where T represents the linear tension of the textile in the circumferential direction and c the curvature of the leg to which the compression is applied.

There has been produced in this way a three-dimensional map simulating the compression pressures that the orthosis would apply to the surface of the leg if it were threaded over the latter.

This map can advantageously be displayed in graphical form in different ways, as will be explained with reference to FIGS. 4 to 8, which represent diverse displays presented to the practitioner to assist him in prescribing or in his clinical study.

It is in particular possible to display a three-dimensional representation 52 of the leg (FIG. 4), with the facility for the practitioner of turning the leg, selecting a point, zooming into a portion of the leg, etc. The representation 52 is advantageously coded in grey levels or in false colours against a reference scale 54 for evaluating the level of the applied pressure (for example blue for a weak pressure, green for a moderate pressure, yellow for a high pressure, red for a very high pressure). The pressure scale 54 extends from the minimum calculated value to the maximum calculated value, but it is possible to modify it to show finer detail for a particular pressure area.

The practitioner can equally designate a particular point 78, for example by means of a mouse and a graphical interface, in order to display in a values area 64 (FIG. 1) the numerical values associated with that precise point: coordinate, curvature, pressure, etc.

Moreover, the device also calculates the average values of the pressures exerted at the various points of the same contour at a given coordinate, enabling display of a pressure profile 56 as a function of the coordinate (FIG. 5). The designation of the point 78 on the FIG. 4 representation is transferred to the point 80 on the FIG. 5 profile, for example by an area of a different colour, providing an immediate visualization of the pressure level corresponding to the coordinate of the point 78.

To evaluate the distribution of the pressures exerted at the various points of a given section, the practitioner also can use a two-dimensional visualization (FIG. 6) representing a section 58 of the leg at a constant coordinate. Here again, the pressure levels are coded by means of a scale of grey levels or false colours 60 and the point 78 designated in the FIG. 4 representation is also repeated in this two-dimensional view (the various displays are all interdependent, so that any modification of the coordinate of the point 78 by the operator automatically modifies the level of the section 58).

Moreover, a graph 62 (FIG. 7) gives the variation as a function of angle of the pressure on the leg section shown in FIG. 6: each bar of the bar chart 62 represents a point of the section, the selected point 78 being represented by a bar 92 of a different colour.

Finally, and generally, it is possible to effect a partial selection by defining an angular area of interest. The angular sector of the leg that is not selected could be indicated in a particular manner on the displays, for example by a greyed out area.

The invention claimed is:

1. A device for assistance in the selection of a therapeutic tubular compression orthosis made from an elastic material and in adapting same to the morphology of a limb for which the orthosis is intended, characterized in that it comprises:
   means (26) for establishing a first file
   containing data representative of the morphological characteristics of the limb (30), this first data file comprising the coordinates, in a three-dimensional space, of a array of points (68) distributed on the surface of the limb along a succession of contours (66) defined at different successive coordinates (Z) of that limb;
   means (10) for establishing a second file
   containing data representative of the dimensional and rheological characteristics of the orthosis defined at different successive coordinates (Z) of that orthosis and giving the elongation of the orthosis resulting from the tension orthosis;
   compression simulation means (48) able to calculate the compression pressure at a plurality of points (68) of said array from data contained in the first and second files by application of Laplaces's law at the plurality of points as a measure of compression on the limb (30) by the orthosis (70) if applied over the limb; and
   means (50) for displaying said pressure values determined by the compression simulation means.

2. The device of claim 1, wherein the second data file contains data for the flat width ($L_0$) of the orthosis at said successive coordinates and data ($\Delta x/\Delta f$) representative of the deformation characteristic of the orthosis as a function of the tension exerted thereon between points situated at consecutive coordinates.

3. The device of claim 1, further comprising designation means enabling an operator of the device to designate a point of the array and to command the pressure value display means to display the value of the pressure calculated at the designated point (78).

4. The device of claim 1, further comprising designation means enabling an operator of the device to designate a coordinate of the array and to command the pressure value display means to display the pressure value calculated at the various points of a contour of a cross-section of the limb situated at the designated coordinate (78).

5. The device of claim 1, wherein the display means comprise graphical means able to display a two-dimensional graphical representation (58) of a cross-section of the limb and to associate locally with that graphical representation the pressure values calculated at the various points of a contour of the cross-section.

6. The device of claim 1, wherein the display means comprise graphical means able to display a three-dimensional graphical representation (52) of the limb and to associate locally with that graphical representation the pressure values calculated at the various points of said array.

7. The device of claim 5, wherein the graphical means associate the calculated pressure values with the graphical representation by superimposing a coding by grey levels or false colours of the pressure calculated at those points on said graphical representation at the location of the various points.

8. The device of claim 1, wherein the display means comprise graphical means able to display a characteristic (62) giving a variation, as a function of angular position, of the pressure calculated at the various points of a contour of a cross-section of the limb situated at a given coordinate.

9. The device of claim 1, wherein:
   the simulation means are also able to determine average values of the compression pressure at points situated at the same coordinate, and
   the display means comprise graphical means able to display a characteristic (56; 80) giving a variation, as a function of the coordinate, of the calculated mean compression pressure.

\* \* \* \* \*